United States Patent [19]
Shouldice et al.

[11] Patent Number: 5,824,881
[45] Date of Patent: Oct. 20, 1998

[54] GAS/FLUID DETECTOR FOR CONTAINED FLUID SYSTEMS

[75] Inventors: David Shouldice, Lakewood; Coy Vann Toavs, Boulder, both of Colo.

[73] Assignee: COBE Laboratories, Arvada, Colo.

[21] Appl. No.: 713,758

[22] Filed: Sep. 13, 1996

[51] Int. Cl.$^6$ ................................................. G01N 33/48
[52] U.S. Cl. ....................... 73/19.1; 73/24.01; 73/24.02; 73/61.49; 73/61.79
[58] Field of Search ................................. 73/19.03, 19.1, 73/24.01, 24.02, 61.44, 61.45, 61.49, 61.79, 64.53

[56] References Cited

U.S. PATENT DOCUMENTS

| | | | |
|---|---|---|---|
| 4,112,740 | 9/1978 | Brandestini | .............................. 73/64.53 |
| 4,280,126 | 7/1981 | White . | |
| 4,316,183 | 2/1982 | Palmer et al. . | |
| 4,340,938 | 7/1982 | Rosso | ................................. 73/61.44 X |
| 4,457,751 | 7/1984 | Rodler . | |
| 4,487,601 | 12/1984 | Lindemann . | |
| 4,630,245 | 12/1986 | Dam | .......................................... 367/93 |
| 4,630,482 | 12/1986 | Traina | ................................. 73/24.01 X |
| 4,673,927 | 6/1987 | Cianciavicchia et al. . | |
| 4,764,166 | 8/1988 | Spani . | |
| 4,784,643 | 11/1988 | Siretchi et al. . | |
| 5,191,795 | 3/1993 | Fellingham et al. . | |
| 5,192,933 | 3/1993 | Rodriguez | .............................. 340/621 |
| 5,382,232 | 1/1995 | Hague et al. . | |
| 5,455,565 | 10/1995 | Moeenziai et al. . | |

FOREIGN PATENT DOCUMENTS

| 4140572 | 6/1992 | Germany | .............................. 73/61.49 |
|---|---|---|---|

*Primary Examiner*—Hezron E. Williams
*Assistant Examiner*—Daniel S. Larkin
*Attorney, Agent, or Firm*—Holme Roberts & Owen

[57] ABSTRACT

The present invention provides an improved gas/fluid detector for use in contained fluid systems, and is particularly apt for medical applications wherein fluids are transfused to a patient. The invention includes directing energy pulses into a fluid containment region of interest, detecting energy at the region of interest during each of a plurality of intervals associated with the energy pulse, generating a multi-component detection output utilizing the detected energy for each of the time intervals and separately employing each of the components of the multi-component detection output to determine whether a predetermined condition exists within the contained region of interest. Such predetermined condition may be one of the absence/presence of fluid/gas. Preferably, a multi-component detection signature is provided in the form of a digital serial output and compared with a reference signature that is provided in a corresponding digital serial output. The reference signature reflects the detection signature that should be generated for the predetermined condition of interest. The invention allows for the utilization of a single acoustic or ultrasonic transducer for pulse transmission and energy detection in a pulse/echo implementation, thereby facilitating a single-sided mount arrangement with disposable fluid-containing structures commonly employed in medical applications.

35 Claims, 3 Drawing Sheets

GAS/FLUID DETECTOR FOR CONTAINED FLUID SYSTEMS

FIELD OF THE INVENTION

The present invention relates to the detection of gases/fluids in contained fluid systems and, more specifically, within fluid containment regions through which fluids pass during normal operations. The invention is particularly apt for detecting the absence/presence of fluids/gases in reservoirs and tubing lines employed in medical-related devices, such as those utilized in transfusing fluids to patients (e.g., the return of blood components in extracorporeal blood processing and blood therapy systems).

BACKGROUND OF THE INVENTION

It is common in many medical and industrial applications to monitor the absence/presence of fluids/gases within contained fluid systems. Such monitoring can be employed for system control and safety purposes, and must typically operate with a high degree of reliability.

Numerous medical applications employ detection systems to detect the absence/presence of fluid/air in tubing lines or at one or more predetermined levels within reservoirs containing fluids for transfusion to patients, including for example, extracorporeal blood processing and blood therapy systems. In such applications, detection systems can be employed to reduce the risk of air transfusion to the patient. Relatedly, detection systems can also be employed for control purposes (e.g., pump control) in non-continuous or cyclical fluid transfer applications, including, for example, single-needle, extracorporeal blood processing and blood therapy applications that utilize reservoirs in which blood components cyclically accumulate within and are removed from during normal operations.

Known detection systems employ radiation or ultrasonic energy transmission into and energy detection at the fluid containment region of interest, and rely upon the transmissivity differences between the relevant fluids and/or gases to be detected. By way of example, in typical ultrasonic systems the detection of transmitted energy at a predetermined minimum intensity will indicate the presence of fluid within the corresponding fluid containment region.

Such a detected state may be considered the "positive" condition for system design. That is, the system is designed to require the positive detected condition for pump operation to transfuse fluid to the patient. Conversely, in the absence of such a positive detected condition (i.e., the "negative" or default condition), the system is designed to terminate fluid passage to a patient.

As will be appreciated, regardless of the system design approach, it is important to reduce the incidence of false positives/negatives, i.e., detector output falsely indicating a given condition in the contained region of interest. Such false indications most typically result from system component misoperation/failure or environmental influences.

To address these sources of false positives/negatives, known detection systems have employed redundant detection componentry (e.g., by employing plural ultrasonic transducers) and/or environmental shielding components (e.g., electromagnetic interference shielding). Such approaches to the problem have component cost and user convenience implications.

SUMMARY OF THE INVENTION

It is an object of the present invention to provide a highly reliable system for detecting a predetermined fluid/gas condition within a contained region of interest, such as the presence/absence of fluids/gases in reservoirs and tubing lines used in medical applications involving fluid transfusion to a patient.

Another object of the present invention is to provide a highly reliable detection system that reduces redundant detection and environmental shielding componentry.

A further object of the present invention is to provide a highly reliable detection system in a manner that allows for virtual fail safe design, that is, in a manner that allows for exponential reduction in any probabilistic false negative/positive occurrence.

Still another object of the present invention is to provide a highly reliable detection system that combines fail safe features with redundant features for reduced component cost.

An additional object of the present invention is to provide a highly reliable detection system, while also increasing operator convenience and, more particularly, which allows for convenient, single-sided mount engagement between the fluid containment structure and detection system componentry.

These and additional objectives are realized in the present invention by directing energy pulses into a fluid containment region of interest, detecting energy at the region of interest during a plurality of time intervals associated with each given energy pulse, and generating a multi-component, time-based detection output separately using the detected energy corresponding with each time interval for each energy pulse. The multi-component, time-based output, or "detection signature," can be employed to determine whether a predetermined condition exists within the contained region of interest, such predetermined condition being one of the presence/absence of gases/fluids.

More particularly, the multi-component detection signature corresponding with each energy pulse can be compared to a predetermined, multi-component "reference signature" to yield a highly reliable detection technique. In this regard, the reference signature reflects the detection signature output that would be expected for a given predetermined condition of interest. Specifically, for example, the multi-component reference signature may include one or more components that correspond with the time intervals following a given detection energy pulse during which energy at a given predetermined level should be detectable if a given predetermined condition exists within the region of interest. Such time interval and predetermined energy level will, of course, depend in each implementation upon the expected (i.e., design basis) energy pulse travel path from the pulse transmission means to the energy detection means. In turn, the travel path will largely depend upon the acoustic impedances and resultant acoustic impedance mismatches at the boundaries of the materials (e.g., fluid, gas, containment structure) encountered by the energy pulse when the predetermined condition of interest exists.

By generating/employing multi-component detection and reference signatures, enhanced reliability is exponentially realized since, if any one component of the multi-component, detection signature output for a given energy pulse does not "match" with the corresponding component of the reference signature, the corresponding predetermined condition should not be detected. For example, in an arrangement where the multi-component detection and reference signatures each comprise an eight-bit serial pulse train, each bit corresponds to a single "component" of the signature. If the detection signature differs in only one bit position from the reference signature, then the predetermined condition is not detected. Because there are eight bits in the detection signature, there is only a one in 28 or 1/256 probability that the predetermined condition will be falsely detected by random error in the system. If a greater number of bits are used in the signatures, an even lower probability of mistaken detection exists. Redundant reference signal comparisons and repeated testing further allow for reduction of any probabilistic occurrence of mistaken detection, as will be further discussed.

The predetermined condition may include, for example, a "fluid condition" wherein the fluid containment region of interest is filled with a fluid, such as blood. If the region is not filled, such as when there is air or air bubbles in the region, the fluid condition should not be detected and system operation can be halted.

Upon comparing the detection signature and reference signature, a resultant first comparison output can be generated for use by a first processing means to identify the presence/absence of the predetermined condition and, additionally, to provide an appropriate control signal responsive thereto. Such control signal may, for example, serve to initiate, terminate or otherwise control the rate of blood passage through the fluid containment region of interest by initiating, terminating or controlling one or more fluid pump means.

In one aspect of the present invention, the detection and reference signatures are both generated in the form of digital outputs, thereby facilitating comparison of each signature component on a substantially real-time basis. For example, a serial detection signature can be progressively generated by deriving an amplitude-related value from the detected energy for each successive time interval associated with a given pulse, and successively comparing the derived values with a predetermined amplitude-related value that reflects a minimum amplitude of energy that should be detectable at the region of interest if the predetermined condition of interest exists (e.g., the presence of fluid). The serial detection signature may then be compared on a bit by bit basis with a serial reference signature or it may first be converted to parallel form and then compared with a parallel reference signature.

In another aspect of the present invention, a pulse/echo detection technique is utilized wherein a single transducer is positioned adjacent to the fluid containment region of interest for both transmitting energy pulses and detecting corresponding echo pulses. By way of primary example, such transducer means may be an acoustic or ultrasonic transducer that can be readily coupled to an outside surface of a reservoir, tubing line or other structure defining the fluid containment region of interest. In medical applications, such structures are typically replaced after each patient usage, and therefore the ability to easily load/unload the same provides significant operator advantages.

In yet another aspect of the present invention, redundant first and second reference signature outputs are provided by redundant reference signature generators. The redundant reference signature generators may include, for example, a counter circuit having a reference clock input synchronized with the drive pulse or it may include a memory means for storing valid reference signatures and for synchronously outputting the reference signatures for comparison purposes. Such redundant generators avoid the cost and user utility implications associated with redundant energy detection componentry and otherwise reduce the risk of a false positive detection of a predetermined condition within the region of interest that could otherwise result upon misoperation/failure of a reference signature generator if only a single reference signature generator were employed.

In this regard, the second predetermined reference signature output can be compared with the detection signature output to generate a second comparison output for use by a second processing means. Such second processor may employ the second comparison signal to control a safety system that may terminate the operation of one or more selected pumps or other system components should a first processing means fail to do so when a predetermined condition is/is not detected.

In still another aspect of the present invention, testing may be performed to determine whether a component failure has occurred by temporarily replacing the reference signature with a testing signature that is different from the reference signature. If the first comparison output indicates that the predetermined condition exists prior to initiation of the test, the replacement of the reference signature with the testing signature should change the first comparison output to indicate the non-existence of the predetermined condition if there are no component failures. If the first comparison output does not change during testing, a component failure has been detected. Redundant testing may be performed to ensure that the redundant capabilities of the present invention are maintained.

In yet another aspect of the present invention, a plurality of timing windows are defined after the occurrence of a drive pulse and a signal is generated that indicates which timing windows are coincident with the reception of a return pulse and which timing windows are not. The signal may then be compared to a reference signal indicative of the existence of a predetermined condition. To add redundancy to the system, the signal may be compared to the reference signal using two separate comparison means. By defining timing windows and determining which windows are/are not coincident with the reception of a drive pulse, the invention reduces the probability of mistaken detection by limiting the number of errors that can result in false detection.

As noted, the present invention is particularly apt for medical applications since it is highly reliable, responsive and capable of implementation in a manner facilitating easy coupling between a detection system and fluid containment structure. Such structures may include, for example, molded plastic reservoirs, tube fittings, and flexible tubing lines which allow for pulsed energy transmission/detection therethrough. In this regard, the invention is capable of detecting undesired air bubbles and foam conditions with such structures.

In one medical implementation, two separate assemblies, which each embody the present invention while sharing common processing means, can be utilized to detect and thereby control the collection and removal of blood components in a reservoir for transfusion to a patient (e.g., in a single-needle apherisis system). In such an implementation, the pulsed transmission means and detecting means of the first assembly, any position adjacent to a bottom portion of the blood component reservoir for low-level fluid detection wherein a fluid-return-to-patient pump stoppage is effected upon the failure to detect fluid in the bottom portion. The pulsed transmission means and detecting means of the second assembly are positioned adjacent to an upper portion of the blood component reservoir to provide for upper-level fluid detection wherein, for example, fluid-return-to-patient pump initiation is effected upon the detection of fluid in the upper portion. Further implementations of the invention will be apparent to those skilled in art.

DETAILED DESCRIPTION

Figure 1:
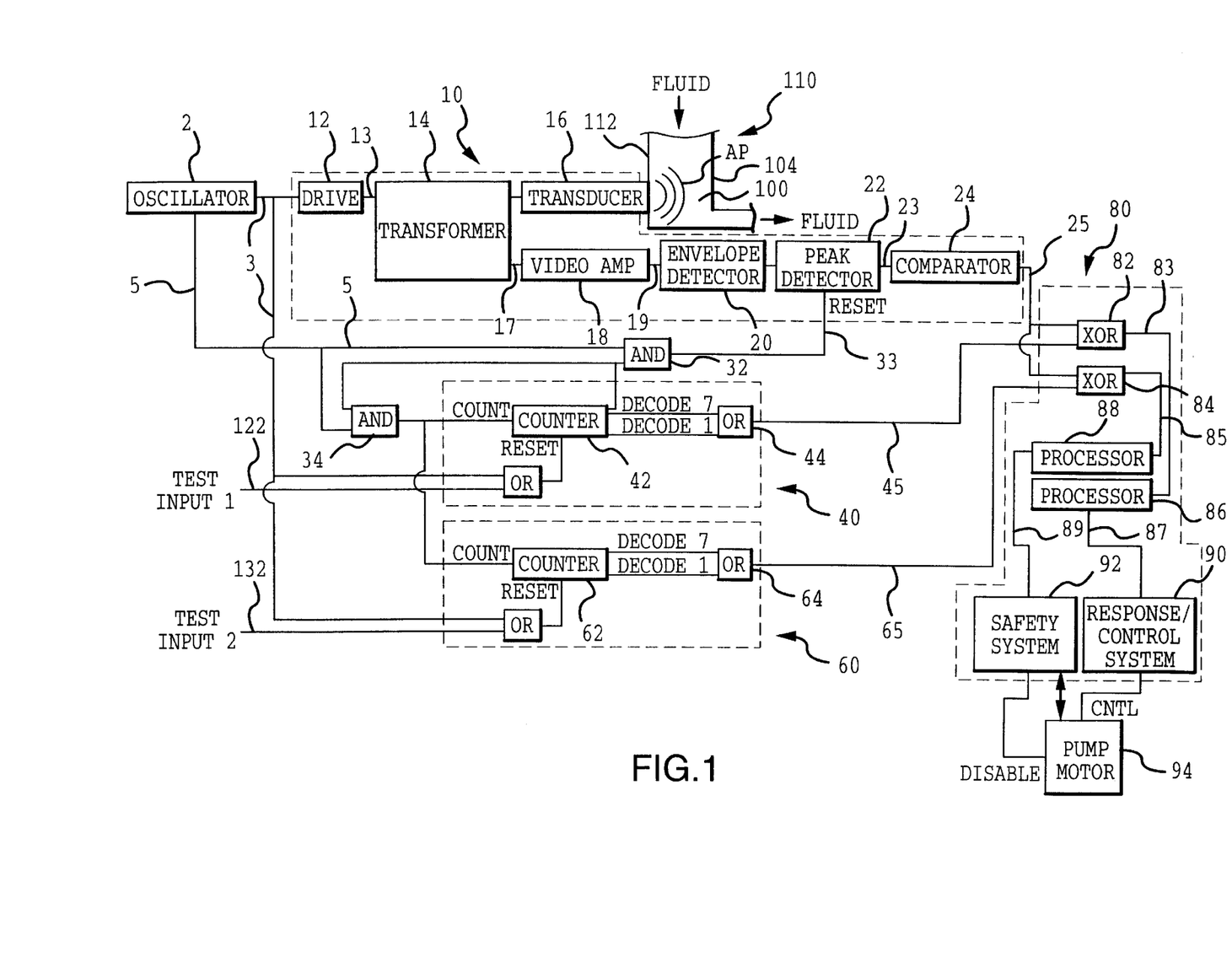
FIG. 1 is a schematic illustration of a pulse/echo embodiment of the present invention.
Figure 2:
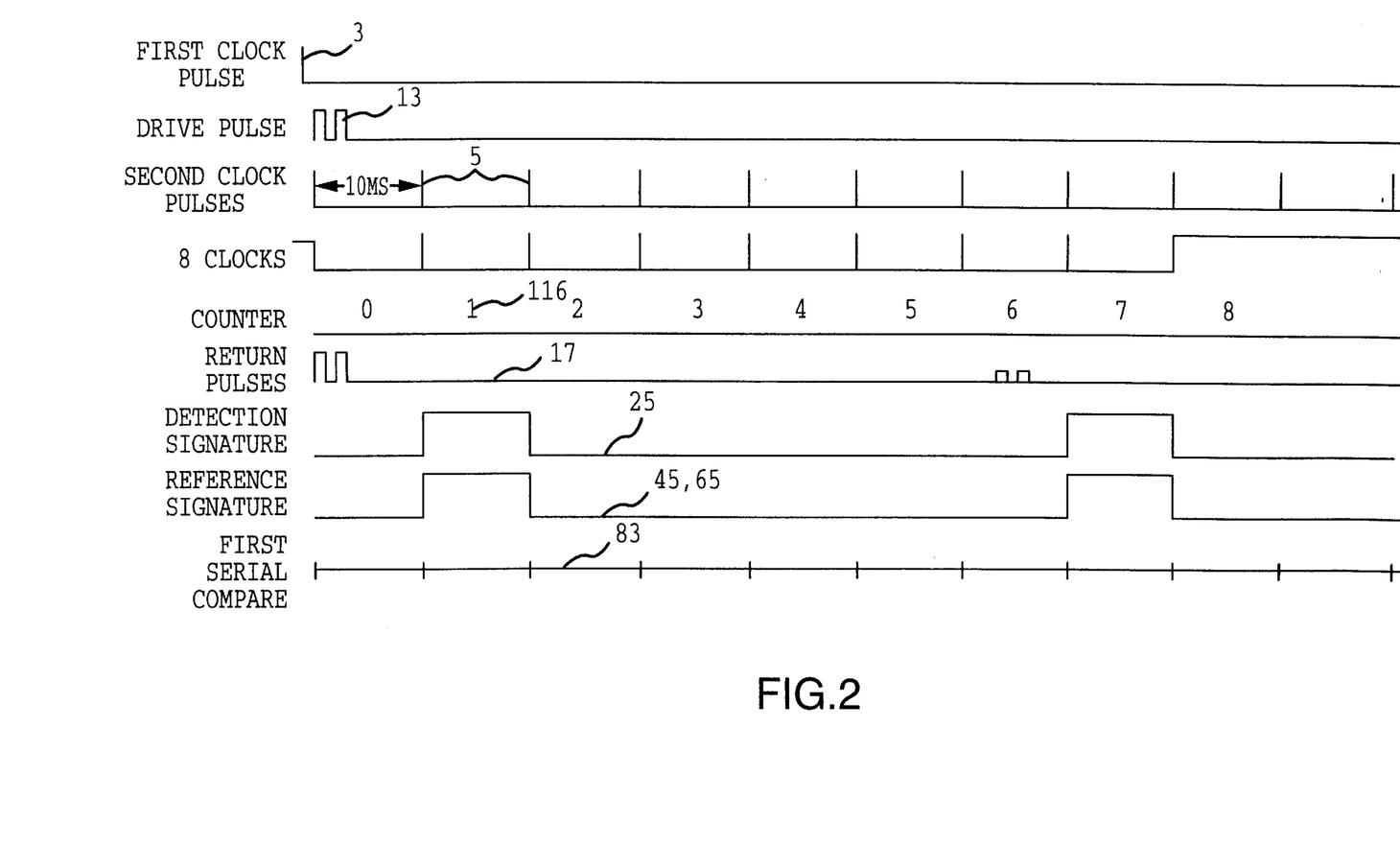
FIG. 2 is a timing diagram pertaining to an exemplary implementation of the embodiment of FIG. 1.

FIGS. 1 and 2 pertain to an pulse/echo embodiment of the present invention. As illustrated in FIG. 1, the embodiment generally includes an oscillator 2, a detection signature generator 10, redundant first and second reference signature generators 40 and 60, respectively, and a control output generator 80.

Broadly, oscillator 2 provides a first clock pulse 3 each period T and a plurality of second clock pulses 5 within each period T. Responsive to first clock pulse 3, detection signature generator 10 transmits an acoustic or ultrasonic energy pulse AP into a fluid containment region of interest 100, detects acoustic or ultrasonic energy at the fluid containment region 100 during each of a plurality of time intervals N associated with the acoustic or ultrasonic energy pulse AP, including detectible echo pulses, and utilizes the detected energy for each time interval N to generate a serial digital detection signature output 25. Redundant first and second reference signature generators 40 and 60 each utilize the first and second clock pulses 3 and 5 to generate first and second serial digital reference signature outputs 45 and 65. Reference signature outputs 45 and 65 should correspond with the output that would be expected from detection signature generator 10 for a given predetermined condition within the containment region (e.g., the presence of fluid). The control output generator 80 receives the first and second reference signature outputs 45 and 65, respectively, as well as detection signature output 25, and generates first and second control outputs 87 and 89 for use in response/control system 90 and safety system 92, respectively.

In the embodiment shown, detection signature generator 10 includes a drive 12 for generating electrical drive pulses 13 which are transformed into acoustic or ultrasonic pulses and directed into the fluid containment region of interest 100 by transformer 14 and transducer 16. The transducer 16 is coupled (e.g., by pressure engagement) to an outside wall 112 of a fluid containment structure 110 defining the region of interest 100. The transducer 16 also receives acoustic or ultrasonic energy at the fluid containment region 100, including detectable echo pulses that have travelled through the region of interest 100, reflected at opposing wall 104, and returned to transducer 16. The detected energy is included in the output 17 from transformer 14, and such output 17 is amplified by a video amplifier 18. Envelope and peak detectors 20 and 22, respectively, then derive (e.g., via sampling) values corresponding with maximum energy amplitudes during each of the predetermined time intervals N. As will be further explained, time intervals N are provided to peak detector 22 via pulsed signal 33. The output 23 of peak detector 22 corresponding with each of the N time intervals is compared by comparator 24 with a predetermined amplitude-related value to yield the digital serial detection signature 25. For example, if the maximum derived amplitude for a given time interval exceeds the predetermined value (e.g., indicating the receipt of an echo pulse), comparator 24 would provide a digital output of "1." Conversely, if the maximum desired amplitude for a given time interval is less than the predetermined value, comparator 24 would output a "0." The serial output of comparator 24 forms the detection signature.

As will be appreciated, while the present invention advantageously allows for the use of a single transducer 16 in a pulse/echo implementation, plural transducers may also be employed for transmission/detection of energy pulses in other arrangements. The use of a single transducer 16 accommodates single-sided mounting of a reservoir, tubing or other structure 110 relative to the transducer 16, thus facilitating loading/unloading operations. This is of particular advantage in medical applications where fluid-containing structures are most typically disposed of on a single-use, patient-by-patient basis.

Returning to FIG. 1, it can be seen that first and second reference signature generators 40 and 60 each include a corresponding counter 42 and 62 for receiving first and second clock pulses 3 and 5. As will be further explained, each counter 42 and 62 has two predetermined output pins interconnected to a corresponding OR gate 44 and 64, respectively, to provide the first and second serial digital reference signature outputs 45 and 65. In each case, first clock pulses 3 serve to reset each counter 42 and 62 each period T and second clock pulses 5 serve to drive the counting function of counters 42 and 62. By providing first and second reference signature generators 40 and 60, redundant safety functionality is provided to reduce any risk that a false positive/negative could occur in the event of failure/malfunction of either reference signature generator 40 or 60.

In one application of the illustrated embodiment, as illustrated by the timing diagram of FIG. 2, first clock pulses 3 are provided each 100 milliseconds, second clock pulses 5 are provided each 10 microseconds, and N=8 (i.e., eight time intervals are defined for comparate energy detection) to thereby provide for an eight-bit serial signature output from each of the detection signature generator 10 and first and second reference signature generators 40 and 60. Such eight-bit signatures readily accommodate, of course, current digital processing.

In such application, counters 42 and 62 may be Johnson decade counters. Since $T/t \neq N$ and since decade counters 42 and 62 have more than N output pins, AND gate 32 and AND gate 34 are utilized in the manner illustrated to provide clock pulses 33 to peak detector 22, and to lock the Nth output pin of counters 42 and 62 high and suspend counting until counters 42 and 62 are reset by first clock pulse 3.

In the application illustrated by the timing diagram of FIG. 2, an echo pulse should be detectable only in the seventh interval if fluid is present in the fluid containment region of interest 100. In such application, the serial detection signature output 25 should be 10000010, wherein a 1 is generated during the first interval due to the drive pulse. As illustrated in FIG. 2, there is a delay of one clock cycle between the time a return pulse is received and the time a detection signature pulse is generated due to delays in the generation and reception of the acoustic or ultrasonic energy pulse AP. To provide corresponding reference signature outputs 45 and 65, the first and seventh decode outputs from decade counters 42 and 62 are connected to OR gate 44 and OR gate 64, respectively.

As shown in FIG. 1, control output generator 80 includes a first XOR gate 82 for receiving serial detection signature output 25 and first reference signature output 45, and responsively providing first serial compare output 83. Since the detection signature output 25 should be identical to the first reference signature output 45, as illustrated in FIG. 2, if the corresponding predetermined condition exists within the fluid containment region of interest 100, the serial compare output 83 of XOR gate 82 should, for example, be 0. If the predetermined condition is not detected, the serial compare output 83 should include at least one 1 for a given signature output. The first compare output 83 is provided to first processor 86 for identifying when the predetermined condition is/is not detected and for providing a responsive control output 87 to response/control system 90, wherein the operation of one or more selected pumps 94 or other system components may be selectively terminated, initiated, or otherwise controlled (e.g., by controlling the rate of blood transfer effected thereby).

The control output generator 80 further includes XOR gate 84 for receiving serial detection signature output 25 and second reference signature output 65 and responsively providing second serial compare output 85. A second processor 88 receives the second compare output 85 for identifying when the predetermined condition is/is not detected and for providing a responsive control output 89 to safety system 92. If control output 89 indicates that the predetermined condition is not being detected, safety system 92 checks the pump motor 94 to determine whether it is currently operating. If the pump motor 94 is operating, the safety system waits for a predetermined time interval to elapse (to allow time for the response/control system to turn off the motor 94) and then disables the pump motor 94. If the pump motor 94 is not operating, the safety system monitors the pump motor 94 to ensure that it remains off until safe operating conditions have been restored. In this way, two separate (i.e., redundant) mechanisms exist for terminating operation of the pump motor 94 when the predetermined condition is not detected.

For system testing purposes, the illustrated embodiment further includes first and second test inputs 122 and 132, corresponding with first and second reference signature generators 40 and 60, respectively. The first and second test inputs 122 and 132 enable testing of the detection signature generator 10 and first and second reference signature generators 40 and 60. Even though a single failure in one of the reference signal generators 40, 60 will not generally result in an undesired operational state for pump motor 94 (due, in part, to the redundancy of the system), it is still desirable that the component failure be detected so that full redundant operation may be restored.

In the illustrated embodiment, testing is initiated during a period when both serial compare outputs 83, 85 indicated detection of the predetermined condition (i.e., the outputs comprise all zeros). During testing, test inputs 122 and 132 are provided to the first and second reference signature generators 40 and 60, respectively, causing decade counters 42 and 62 to be constantly maintained in a reset state, such that the outputs of the decade counters 42 and 62 are comprised of all zeros. Consequently, the outputs of the OR gates 44 and 64 are comprised of all zeros during a test procedure. The test inputs 122 and 132 may, for example, be provided by the processors 86 and 88, respectively, during a random, periodic, or operator requested test procedure. When the outputs of OR gates 44 and 64 are compared to the detection signature output 25 from detection signature generator 10 in exclusive OR gates 82 and 84, respectively, the predetermined condition should not be detected because the detection signature output 25 should include at least one 1 (due to the drive pulse). If the system is operating properly, the processors 86 and 88, which are aware that a test is being performed, detect that the serial compare outputs 83, 85 have changed from a detection to a non-detection state and allow the system to continue operating. If either of the serial compare outputs 83, 85 do not change state during a test, however, the processors 86, 88 detect that at least one component failure exists in the system that must be addressed before fail safe/redundant operation can be restored.

Figure 3:
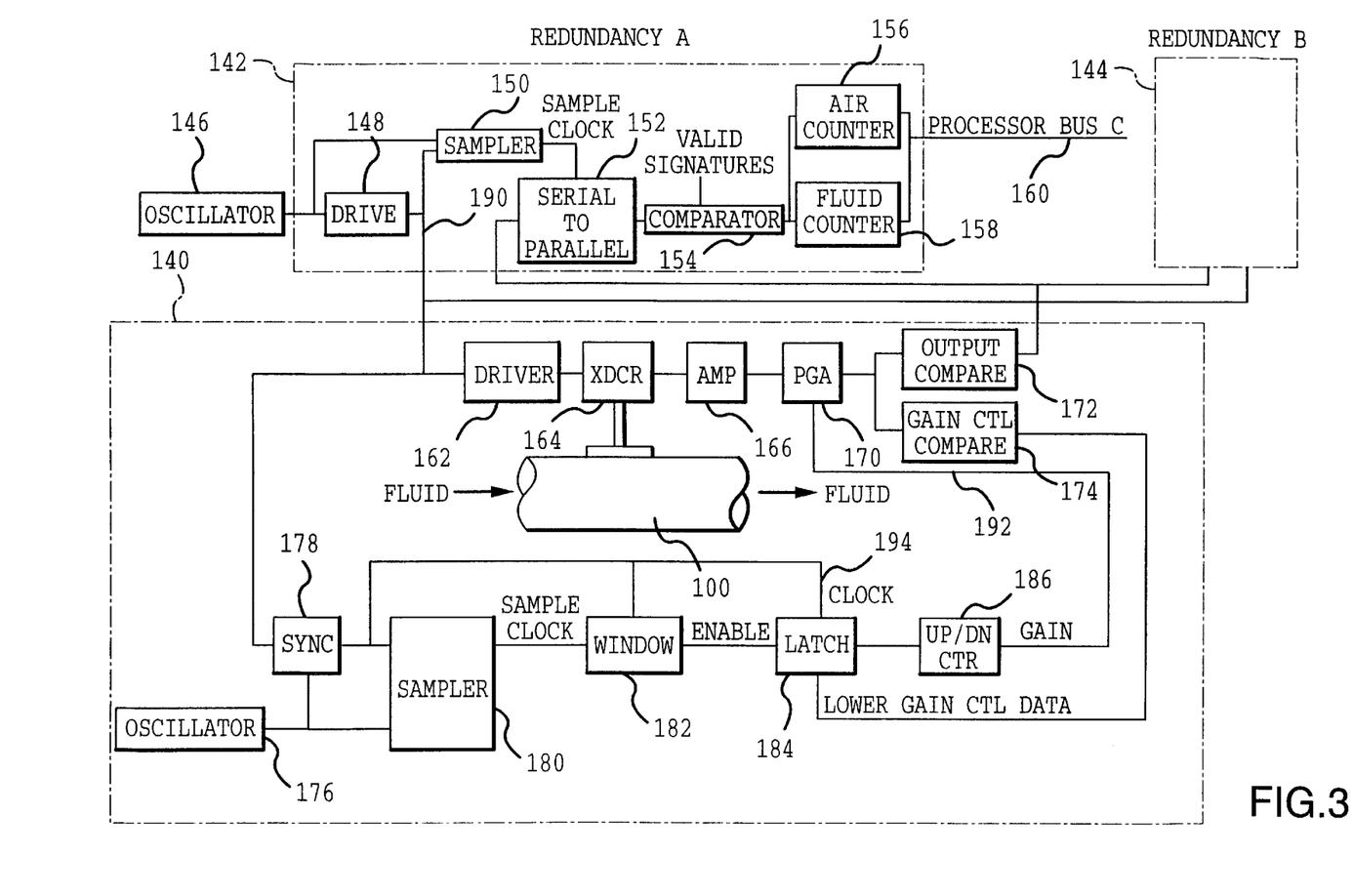
FIG. 3 is a schematic illustration of another pulse/echo embodiment of the present invention.

FIG. 3 illustrates another pulse/echo embodiment of the present invention. The embodiment includes a detection signature generator 140 for generating the detection signature and a pair of redundant comparison circuits 142, 144 for, among other things, redundantly performing the required comparisons with one or more reference signatures. In addition, an external oscillator 146 is provided for creating a timing base to be used by other elements within the system. As illustrated in FIG. 3, the detection signature generator 140 includes: driver 162, acoustic or ultrasonic transducer 164, amplifier 166, programmable gain amplifier (PGA) 170, output comparison unit 172, gain control comparison unit 174, oscillator 176, synchronization unit 178, first sampler 180, window generator 182, latch 184, and up/down counter 186. The first redundant comparison circuit 142 includes: drive unit 148, sampler 150, serial to parallel converter 152, comparator 154, air counter 156, and fluid counter 158. The second redundant comparison circuit 144 is substantially identical to the first redundant comparison circuit 142, except that the second circuit 144 does not include a drive unit 148.

Drive unit 148 receives a periodic signal from oscillator 146 and uses the periodic signal to create a timing signal 190 that sets the repetition rate of the drive pulses that will be acoustically or ultrasonically delivered into the fluid containment region of interest 100. The timing signal 190 is used to synchronize the operation of the first redundant comparison circuit 142, the second redundant comparison circuit 144, and the detection signature generator 140 and hence is delivered to each of these units.

The driver 162 within the detection signal generator 140 receives the timing signal 190 from the drive unit 148 and responsively generates properly timed drive pulses to the transducer 164. In response to the drive pulses, the transducer 164 launches acoustic or ultrasonic pulses into the fluid containment region of interest 100. The pulses are eventually reflected within the fluid containment region of interest 100 and returned to the transducer 164 which converts the reflected pulses into electrical output pulses. The amplifier 166 amplifies the electrical output pulses by a predetermined gain factor. The PGA 170 then further amplifies the pulses, according to a gain control signal 192 from up/down counter 186, to an optimal level. The amplified pulses are then delivered to both the output comparison unit 172 and the gain control comparison unit 174.

The gain control comparison unit 174 compares the amplified pulses to a first predetermined reference level for gain control purposes. If a pulse exceeds the first predetermined level, the gain control unit 174 outputs a 1, otherwise the unit 174 outputs a 0. In this manner, the gain control unit 174 delivers a digital pulse stream to the latch 184, wherein each 1 in the stream is indicative of an amplified pulse that exceeds the first predetermined threshold. The latch 184 receives the digital pulse stream and latches the stream to the up/down counter 186 at times determined by clock signal 194 from synchronization unit 178. The up/down counter uses the latched signal to create the gain control signal 192. If no 1's were output by the latch 184, the counter 186 increases the gain of the PGA 170. Similarly, if 1's were output by the latch 184, the counter 186 decreases the gain of the PGA 170.

To create clock signal 194, synchronization unit 178 synchronizes timing signal 190 to a local oscillator 176.

Sampler 180 receives both the clock signal 194 and the signal from the local oscillator 176 to create a slower clock signal synchronized to the drive pulse. The window generator 182 uses the slower clock signal to generate a timing window signal for the occurrence of an echo. The timing window signal is applied to the enable input of the latch 184 so that the latch 184 is only enabled during the window period.

Similar to the gain control comparison unit 174, the output comparison unit 172 compares the amplified pulses from the PGA 170 to a second predetermined reference level that is less than the first predetermined reference level. If a pulse exceeds the second predetermined level, the output comparison unit 172 outputs a 1, otherwise the unit 172 outputs a 0. In this manner, the output comparison unit 172 creates a digital pulse stream that represents the detection signature. The digital pulse stream is delivered to both the first and second redundant comparison circuit 142, 144.

Because operation of both the first and second redundant comparison units 142, 144 is substantially identical, the following description will be limited to only the first unit 142. The serial to parallel converter 152 receives the serial bit stream from the output comparison unit 172 and converts it to a parallel data word. To do this, the serial to parallel converter 152 uses a sample clock from sampler 150. The sampler 150 creates the sample clock using both the periodic signal from the oscillator 146 and the timing signal from the drive unit 148. The comparator 154 receives each parallel data word from the serial to parallel converter 152 and compares it to one or more valid reference signatures on a bit by bit basis. The comparator 154 may include, for example, a content addressable memory (CAM) that is capable of making comparisons with a plurality of valid signatures simultaneously. In one implementation of the present embodiment, each data word is 25 bits in length and there are 4 valid reference signatures. The comparator 154 outputs a single data bit for each detection signature received. The data bit may be, for example, a 1 if a match with a valid signature was found and a 0 if a match was not found. For each detection signature creating a match, the fluid counter 158 will be incremented by one. Similarly, for each detection signature that does not create a match, the air counter 156 will be incremented by one. The counts from the air counter 156 and the fluid counter 158 can then be downloaded onto bus 160 for analysis by a processor (not shown). The processor can then make system operation decisions based on the counts.

The foregoing discussion of some embodiments of the invention has been presented for purposes of illustration and description. The description is not intended to limit the invention to the embodiments described. Variations and modifications commensurate with the above teachings and apparent to those skilled in the art are intended to be within the scope of the present invention.

What is claimed is:

1. A method for detecting a predetermined condition within a fluid containment region of interest, said predetermined condition being one of the presence or absence of one of a fluid or gas within said fluid containment region of interest, comprising:

directing an energy pulse into the fluid containment region of interest;

detecting energy at the region of interest during each of a first plurality of at least partially non-overlapping time intervals within a predetermined time period associated with the energy pulse;

generating a multi-component detection output utilizing said detected energy, wherein each of said components corresponds with a different one of said first plurality of time intervals;

separately employing each of said components of said multi-component detection output to determine whether said predetermined condition exists within said region of interest.

2. A method, as recited in claim 1, wherein:

said directing step includes:
transmitting said energy pulse from outside said region of interest; and said detecting step includes:
receiving said energy outside said region of interest.

3. A method, as recited in claim 2, further comprising:
utilizing a common transducer means for said directing step and said detecting step.

4. A method, as recited in claim 2, wherein said containment region of interest is defined by a fluid containment structure, and wherein said energy pulse is transmitted from and said energy is received on a common side of the fluid containment structure.

5. A method, as recited in claim 1, said generating step comprising:

providing a digital output corresponding with each of said first plurality of time intervals, based upon said corresponding detected energy, wherein said multi-component detection output is in a binary form; and serially outputting said multi-component detection output.

6. A method, as recited in claim 5, said providing step comprising:

deriving an amplitude-related value from said detected energy for each of said first plurality of time intervals; and comparing said amplitude-related value for each of said first plurality of time intervals with a predetermined amplitude-related value.

7. A method, as recited in claim 1, further comprising:

providing a first predetermined multi-component output, said components of said first predetermined multi-component output corresponding with said time increments; and wherein said employing step includes:
using said first predetermined multi-component output and said multi-component detection output to generate a first compare multi-component output.

8. A method, as recited in claim 7, further comprising:

generating a control output in response to said first compare multi-component output, wherein said control output is operative for controlling the operation of a predetermined system component based on the content of said first compare multi-component output.

9. A method, as recited in claim 8, further comprising:

producing a second predetermined multi-component output, said components of said second predetermined multi-component output corresponding with said time increments; and wherein said employing step comprises:
using said second predetermined multi-component output and said detection multi-component output to generate a second compare multi-component output; and generating a disable output in response to said second compare multi-component output, wherein said disable output is operative for disabling operation of said predetermined system component based on the content of said second compare multi-component output.

10. A method, as recited in claim 7, further comprising:
testing whether a component failure exists in the system by changing said first predetermined multi-component output and determining the effect of said change on said first compare multi-component output.

11. A method, as recited in claim 10, further comprising:
testing whether a component failure exists in the system by changing said second predetermined multi-component output and determining the effect of said change on said second compare multi-component output.

12. A method as recited in claim 1, said method being employed in a medical application comprising the transfusion of a fluid to a patient, wherein said fluid containment region of interest is defined by at least one of a reservoir structure, a tube fitting and a flexible tubing line.

13. A method as recited in claim 1, said method being for use in a medical application comprising fluid transfusion to a patient, wherein said predetermined condition is at least one of the presence of fluid, air, air bubbles and foam within said fluid containment region of interest.

14. An apparatus for use in detecting the presence/absence of a fluid within a fluid containment region, said apparatus comprising:
means for generating a drive pulse at a first instant in time;
means for defining a plurality of timing windows relative to and synchronized with said first instant in time, said timing windows occurring after said first instant in time;
means for launching said drive pulse into said fluid containment region;
means for receiving at least one reflected pulse from said fluid containment region; and
means, coupled to said means for receiving, for creating a detection signal indicative of which timing windows are and which timing windows are not coincident with the reception of a reflected pulse by said means for receiving.

15. The apparatus of claim 14, further comprising:
first means for comparing said detection signal to at least one reference signal associated with a predetermined fluid condition to create a first comparison output signal indicative of whether said predetermined fluid condition exists.

16. The apparatus of claim 15, further comprising:
second means, separate from said first means, for comparing said detection signal to said at least one reference signal associated with a predetermined fluid condition to create a second comparison output signal indicative of whether said predetermined fluid condition exists.

17. The apparatus of claim 15, wherein:
said predetermined fluid condition comprises the presence of said fluid in said fluid containment region.

18. The apparatus of claim 15, further comprising:
means for generating a control signal based on said first comparison output signal, said control signal for use in controlling the operation of a fluid flow system including said fluid containment region.

19. The apparatus of claim 16, wherein:
said means for creating, said first means for comparing, and said second means for comparing, collectively, have a plurality of failure mechanisms that can result in a false comparison output signal; and
substantially all of said failure mechanisms result in a comparison output signal indicative of the lack of said predetermined fluid condition.

20. The apparatus of claim 14, wherein:
said means for generating said drive pulse includes means for generating a train of drive pulses at periodic intervals.

21. The apparatus of claim 14, wherein:
said means for launching includes transducer means.

22. The apparatus of claim 21, wherein:
said transducer means includes at least one of the following: an acoustic transducer and an ultrasonic transducer.

23. The apparatus of claim 14, wherein:
said means for defining includes clocking means synchronized to said first instant in time, wherein said clocking means produces a clock signal having a plurality of equally spaced peaks that define the boundaries of said timing windows.

24. The apparatus of claim 15, wherein:
said means for receiving includes means for qualifying each received pulse by comparing each said pulse to a predetermined threshold level; and
said means for creating includes means for creating a detection signal indicative of which timing windows are and which timing windows are not coincident with the reception of a qualified reflected pulse by said means for receiving.

25. The apparatus of claim 24, wherein:
said means for creating a detection signal includes means for creating a serial bit stream having at least one bit position corresponding to each of said timing windows in said plurality of timing windows.

26. The apparatus of claim 25, wherein:
said serial bit stream includes at least one first bit position having a first value, said at least one first bit position corresponding to a timing window that is coincident with the reception of a qualified reflected pulse, and at least one second bit position having a second value, said at least one second bit position corresponding to a timing window that is not coincident with the reception of a qualified reflected pulse.

27. The apparatus of claim 25, wherein:
said first means for comparing includes means for comparing said serial bit stream to a reference bit stream associated with said predetermined fluid condition.

28. The apparatus of claim 27, wherein:
said means for comparing said serial bit stream compares said serial bit stream on a bit by bit basis; and
said comparison output signal indicates a lack of said predetermined fluid condition when said serial bit stream differs from said reference bit stream in one or more bit positions.

29. The apparatus of claim 25, further comprising:
means for converting said serial bit stream into a parallel data word; and
means for comparing said parallel data word to one or more reference words associated with said predetermined fluid condition.

30. The apparatus of claim 14, further comprising:
first means for testing for a component failure in said apparatus, said first means for testing including means for comparing said detection signal to a signal other than said at least one reference signal to create a test output signal indicative of whether a component failure has occurred.

31. The apparatus of claim 30, further comprising:

second means for testing for a component failure in said apparatus, different from said first means for testing, said second means for testing including means for comparing said detection signal to a signal other than said at least one reference signal to create a test output signal indicative of whether a component failure has occurred.

32. The apparatus of claim 31, wherein:

said first and second means for testing include said first and second means for comparing, respectively.

33. An apparatus as recited in claim 12, and wherein said fluid containment region of interest is defined by at least one of a reservoir structure, a tube fitting and a flexible tubing line.

34. An apparatus as recited in claim 14, said apparatus being employable in a medical application comprising the transfusion of a fluid to a patient, wherein said fluid containment region of interest is defined by at least one of a reservoir structure, a tube fitting, and a flexible tubing line.

35. An apparatus as recited in claim 34, wherein said fluid containment region of interest corresponds with a predetermined fluid level within a reservoir structure, and wherein said fluid comprises blood components.

\* \* \* \* \*